US011090096B2

(12) United States Patent
Schwab et al.

(10) Patent No.: US 11,090,096 B2
(45) Date of Patent: Aug. 17, 2021

(54) SURGICAL ROD BENDER

(71) Applicant: K2M, Inc., Leesburg, VA (US)

(72) Inventors: Frank Schwab, New York, NY (US); Theo Choi, Arlington, VA (US); Timmon Ark, Falls Church, VA (US)

(73) Assignee: K2M, Inc., Leesburg, VA (US)

( * ) Notice: Subject to any disclaimer, the term of this patent is extended or adjusted under 35 U.S.C. 154(b) by 654 days.

(21) Appl. No.: 15/485,455

(22) Filed: Apr. 12, 2017

(65) Prior Publication Data

US 2017/0290615 A1 Oct. 12, 2017

Related U.S. Application Data

(60) Provisional application No. 62/321,396, filed on Apr. 12, 2016.

(51) Int. Cl.
*A61B 17/88* (2006.01)
*A61B 17/70* (2006.01)
*B21F 1/00* (2006.01)
*B21F 45/00* (2006.01)

(52) U.S. Cl.
CPC ...... *A61B 17/8863* (2013.01); *A61B 17/7001* (2013.01); *B21F 1/002* (2013.01); *B21F 45/008* (2013.01)

(58) Field of Classification Search
CPC . B21D 7/00; B21D 7/02; B21D 7/024; B21D 7/0257; B21D 7/025; B21D 7/06; B21D 7/063; B21D 9/00; B21D 9/08; B21D 11/02; B21D 11/18; B21D 37/12; B21F 1/002; B21F 45/008; A61B 17/7001; A61B 17/8863; B25B 7/00; B25B 7/02; B25B 7/06; B25B 7/12; B25B 9/00
USPC ........ 72/372, 409.01, 409.11, 409.13, 409.2, 72/409.03, 409.04, 409.05; 7/157, 166
See application file for complete search history.

(56) References Cited

U.S. PATENT DOCUMENTS

| 1,369,676 | A | * | 2/1921 | Kusisto | ..................... B25B 7/02 81/304 |
| 2,455,609 | A | * | 12/1948 | Scheib | ............... A61B 17/8861 606/103 |
| 5,649,572 | A | * | 7/1997 | Lile | ......................... B21F 15/04 140/121 |
| 6,644,087 | B1 | | 11/2003 | Ralph et al. | |
| 7,823,856 | B2 | * | 11/2010 | Schwartz | .............. G06F 1/1611 248/442.2 |

(Continued)

Primary Examiner — Teresa M Ekiert
(74) Attorney, Agent, or Firm — Lerner, David, Littenberg, Krumholz & Mentlik, LLP

(57) ABSTRACT

An instrument for bending a surgical rod includes first and second arm assemblies. The first arm assembly includes first and second arms having respective first and second receiving portions configured to receive the surgical rod therein. The second arm assembly includes third and fourth arms having respective third and fourth receiving portions configured to receive the surgical rod therein. The instrument is reconfigurable from an initial configuration in which the first and third receiving portions of the respective first and third arms engage the surgical rod such that transitioning the first and third arms towards each other bends the surgical rod in a first orientation and transitioning the first and third arms away from each other bends the surgical rod in a second orientation opposite to the first orientation.

16 Claims, 5 Drawing Sheets

(56) References Cited

U.S. PATENT DOCUMENTS

| | | | |
|---|---|---|---|
| 8,327,682 B2* | 12/2012 | Haase | B25B 27/146 |
| | | | 72/409.02 |
| 8,506,603 B2* | 8/2013 | McClintock | A61B 17/8863 |
| | | | 606/279 |
| 8,714,427 B2 | 5/2014 | McClintock et al. | |
| 9,095,378 B2 | 8/2015 | Wallenstein | |
| 9,144,447 B2 | 9/2015 | McClintock et al. | |
| 9,186,182 B2 | 11/2015 | Wallenstein | |
| 9,295,494 B2 | 3/2016 | Strauss et al. | |
| 9,421,038 B2 | 8/2016 | Noordeen et al. | |
| 2014/0135841 A1 | 5/2014 | Wallenstein | |
| 2014/0135842 A1 | 5/2014 | Wallenstein | |
| 2014/0135843 A1 | 5/2014 | Barrus | |
| 2014/0135844 A1 | 5/2014 | Ark et al. | |

* cited by examiner

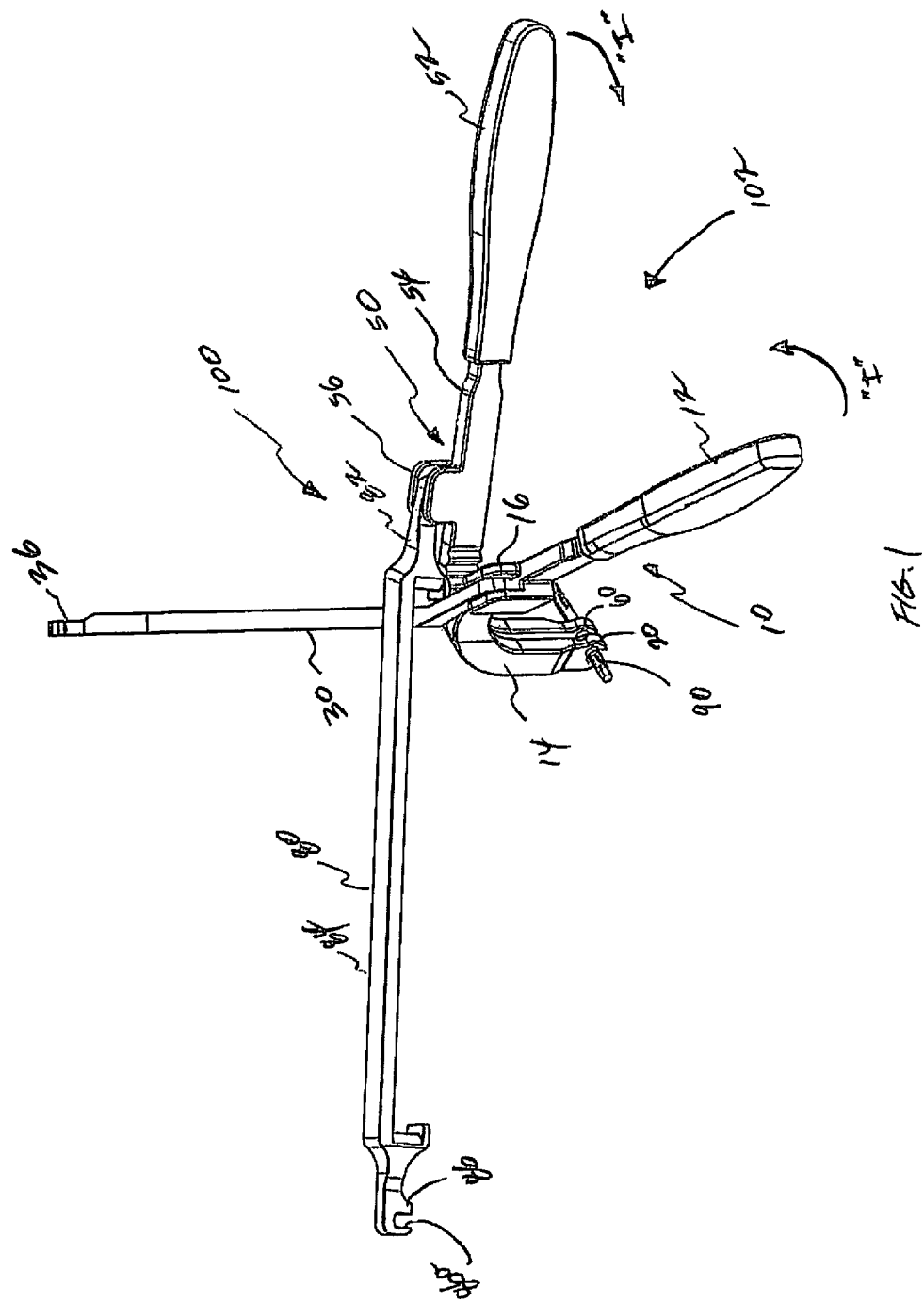

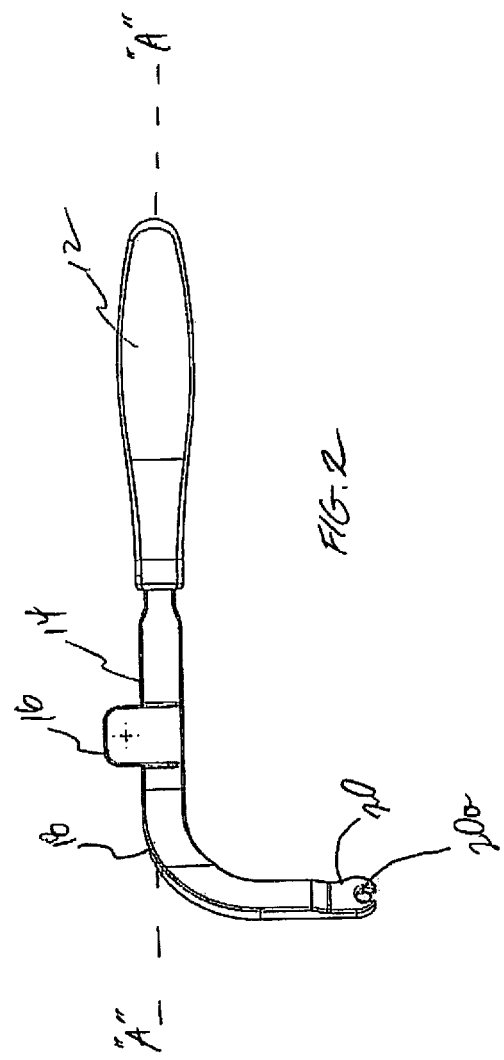
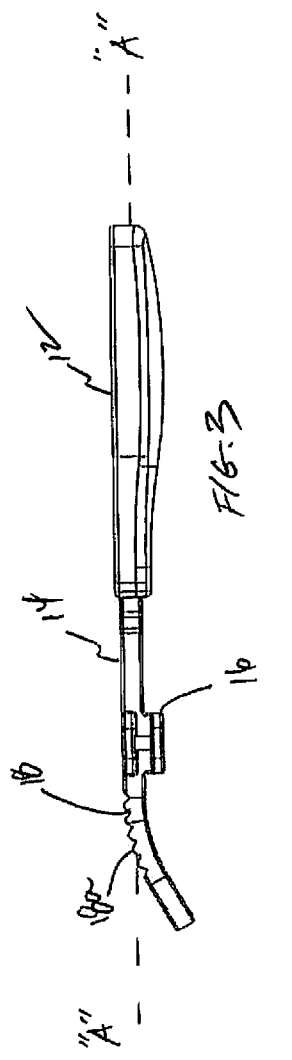

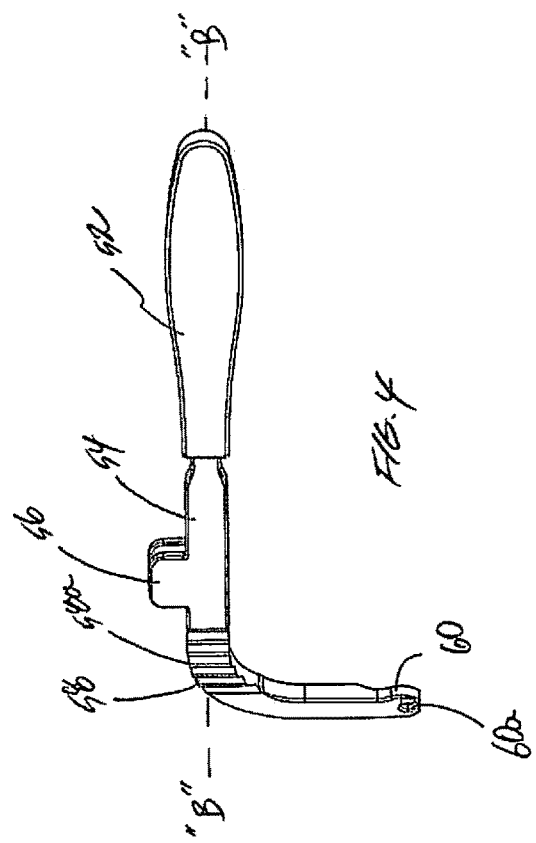
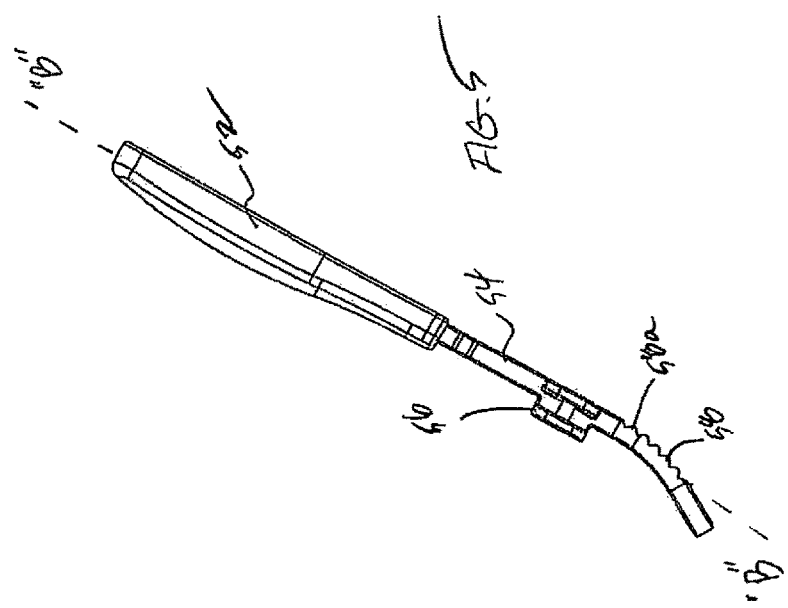

SURGICAL ROD BENDER

CROSS-REFERENCE TO RELATED APPLICATION

This application claims priority to, and the benefit of, U.S. Provisional Patent Application Ser. No. 62/321,396, filed on Apr. 12, 2016, the entire contents of which is incorporated by reference herein.

BACKGROUND

Technical Field

The present disclosure relates to a surgical instrument, and more particularly, to a surgical rod bender.

Background of Related Art

The spine is a flexible structure capable of a large range of motion. There are various disorders, diseases, and types of injury, which restrict the range of motion of the spine or interfere with important elements of the nervous system. The problems include scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function.

Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages, and cadaver and human bone implants. In order to facilitate stabilizing the spine and keeping the interbody in position, other implants are commonly employed, such as spinal rods. Spinal rods are typically made of cobalt chrome, stainless steel, or titanium alloy. However, in order to transition to a less stiff construct at the top, other less rigid materials and rod shapes may be employed to provide the desired stiffness.

Therefore, there is a continuing need for an instrument for bending a surgical rod that can create varying severities or contours of bend in a surgical rod to meet the needs of each patient, while expediting the surgical process.

SUMMARY

In accordance with an embodiment of the present disclosure, there is provided an instrument for bending a surgical rod. The instrument includes first and second arm assemblies. The first arm assembly includes first and second arms. The first and second arms include respective first and second receiving portions configured to receive the surgical rod therein. The second arm assembly includes third and fourth arms. The third and fourth arms include respective third and fourth receiving portions configured to receive the surgical rod therein. The instrument is reconfigurable from an initial configuration in which the first and third receiving portions of the respective first and third arms engage the surgical rod such that spreading of the first and third receiving portions in a first direction bends the surgical rod in a first orientation and spreading of the first and third receiving portions in a second direction bends the surgical rod in a second orientation opposite to the first orientation.

In an embodiment, the first and third receiving portions of the respective first and third arms of the first and second arm assemblies may each define a notch configured to receive the surgical rod therein.

In another embodiment, the surgical rod in the first orientation may define a convex profile. In addition, the surgical rod in the second orientation may define a concave profile.

In an embodiment, the first and third receiving portions in the initial configuration may be in planar contact.

In an embodiment, the first and third arms of the first and second arm assemblies may each include an L-shaped profile.

In another embodiment, the second and fourth arms of the first and second arm assemblies may be hingedly connected to the respective first and third arms of the first and second arm assemblies.

In an embodiment, the first arm of the first arm assembly may further include a handle, and the first receiving portion of the first arm may be offset from a longitudinal axis defined by the handle. In addition, the first and third arms of the respective first and second arm assemblies may include a mating structure to provide incremental spreading of the handles. In particular, the mating structure may include a plurality of teeth.

In accordance with another embodiment of the present disclosure, there is provided an instrument for bending a surgical rod. The instrument includes first and second arm assemblies. The first arm assembly includes a first receiving portion configured to receive the surgical rod therein. The second arm assembly includes a second receiving portion configured to receive the surgical rod therein. The first and second arm assemblies are detachably associated with each other. The instrument is selectively configurable from an initial configuration to a first configuration in which the first and second receiving portions engage the surgical rod for bending the surgical rod in a first orientation and from the initial configuration to a second configuration in which the first and second receiving portions engage the surgical rod for bending the surgical rod in a second orientation opposite to the first orientation.

In accordance with another aspect of the present disclosure, there is provided a method of surgery including providing an instrument for bending a surgical rod including a first arm assembly including a first handle and a first arm extending from the first handle, and a second arm assembly including a second handle and a second arm extending from the second handle. The first and second arm assemblies are detachably associated with each other. The method further includes placing the instrument in an initial configuration in which first and second receiving portions of the respective first and second arms engage the surgical rod such that transitioning the first and second handles towards each other bends the surgical rod in a first orientation and transitioning the first and second handles away from each other bends the surgical rod in a second orientation opposite to the first orientation. The method further includes securing the surgical rod with the first and second receiving portions of the respective first and second arms and bending the surgical rod.

In an embodiment, bending the surgical rod may include transitioning the first and second handles towards each other to create a convex profile in the surgical rod. In another embodiment, bending the surgical rod may include transitioning the first and second handles away from each other to create a concave profile in the surgical rod.

In yet another embodiment, placing the instrument in the initial configuration includes placing the first and second receiving portions of the respective first and second arm assemblies in planar contact.

BRIEF DESCRIPTION OF THE DRAWINGS

The above and other aspects and features of the present disclosure will become more apparent in light of the following detailed description when taken in conjunction with the accompanying drawings in which:

FIG. 1 is a perspective view of an instrument for bending a surgical rod in accordance with an embodiment of the present disclosure illustrating an initial configuration of the instrument;

FIG. 2 is a side view of a first arm of a first arm assembly of the instrument of FIG. 1;

FIG. 3 is a top view of the first arm of the first arm assembly of FIG. 2;

FIG. 4 is a side view of a first arm of a second arm assembly of the instrument of FIG. 1;

FIG. 5 is a top view of the first arm of the second arm assembly of FIG. 4;

DETAILED DESCRIPTION

Figure 6:
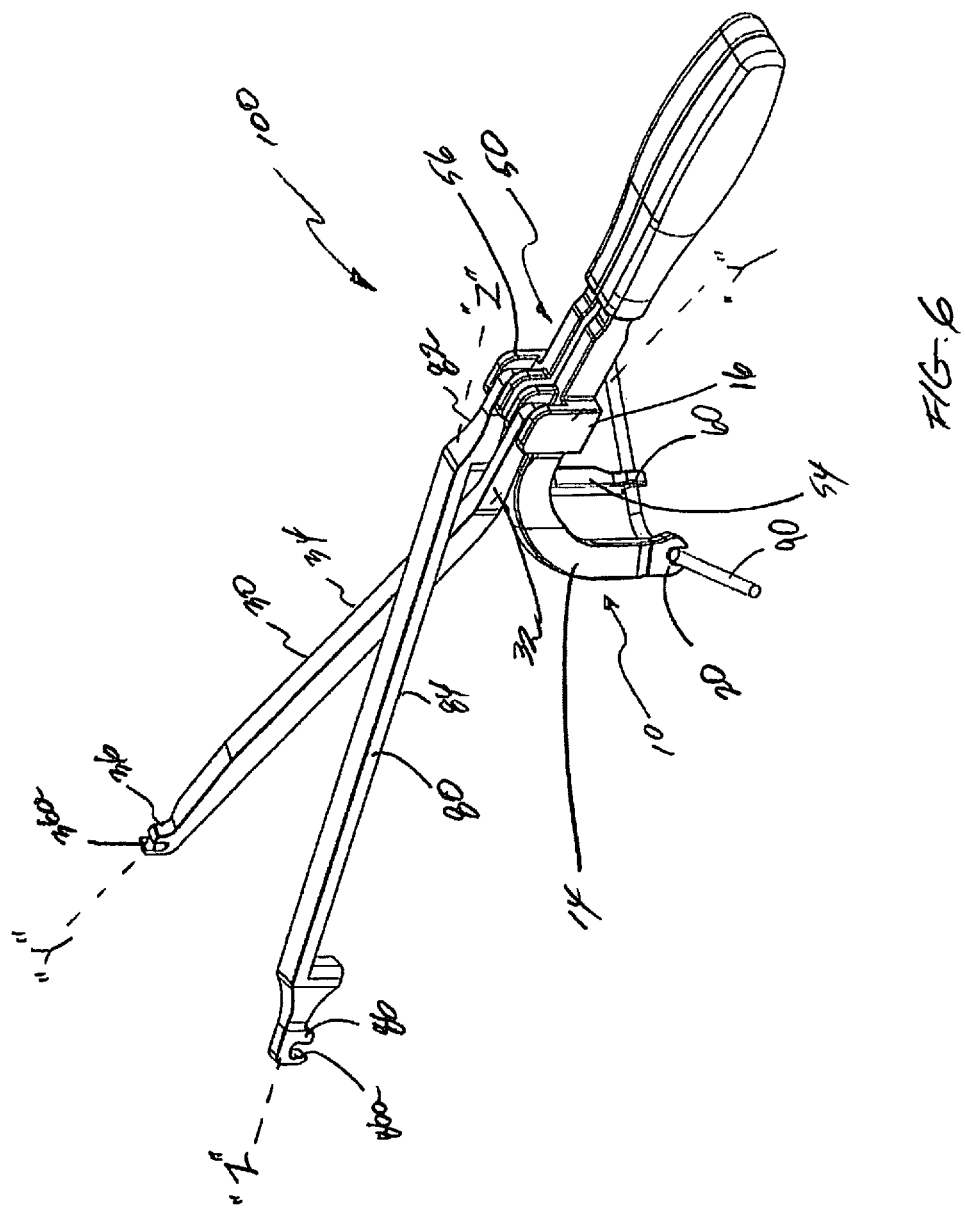
FIG. 6 is a perspective view of the instrument of FIG. 1 illustrating use in a first configuration.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction towards a patient's head, whereas the term "caudad" indicates a direction towards the patient's feet. Further still, the term "medial" indicates a direction towards the middle of the body of the patient, while the term "lateral" indicates a direction towards a side of the body of the patient (i.e., away from the middle of the body of the patient). The term "posterior" indicates a direction towards the patient's back, and the term "anterior" indicates a direction towards the patient's front. In the following description, well-known functions or constructions are not described in detail to avoid obscuring the present disclosure in unnecessary detail.

With reference to FIG. 1, an embodiment of the present disclosure is shown generally as an instrument for bending a surgical rod or a rod bender 100 selectively configurable to create varying severities or contours of bend in a surgical rod 90. For example, rod bender 100 in a first configuration (FIG. 6) may create a convex bend in surgical rod 90, and rod bender 100 in a second configuration (FIG. 7) may create a concave bend in surgical rod 90, as will be described hereinbelow. Rod bender 100 may be utilized prior to fixating spinal rod 90 in a patient, i.e., surgical rod 90 may be bent prior to being inserted in the patient, or in-situ. Rod bender 100 may be made of titanium, titanium alloy, stainless steel, cobalt chrome, a combination thereof, or any other suitable biocompatible material. Surgical rod 90 is utilized to secure vertebral bodies and/or an intervertebral cage interposed between adjacent vertebral bodies to promote spinal fusion. Reference may be made to U.S. Pat. No. 9,295,494, filed on Nov. 8, 2012, entitled "Spinal Stabilization System," the entire content of which is incorporated herein by reference, for a detailed discussion of the construction and operation of a surgical rod.

With reference to FIG. 1, rod bender 100 includes first and second arm assemblies 10, 50. First and second arm assemblies 10, 50 are selectively mated to achieve varying severities or contours of bend such as, e.g., a convex bend (FIG. 6) or a concave bend (FIG. 7), in surgical rod 90. First and second arm assemblies 10, 50 are detachable and may be operatively mated through engagement with surgical rod 90.

With reference now to FIGS. 1-3, first arm assembly 10 includes a handle 12, a first arm 14 extending from handle 12, and a second arm 30 coupled with first arm 14. First arm 14 includes a hinge portion 16. Second arm 30 is hingedly connected with first arm 14 at hinge portion 16. First arm 14 may define a substantially L-shaped profile. First arm 14 further includes an engaging portion 18 having teeth 18a configured to engage a corresponding structure on a first arm 54 of second arm assembly 50 to enable stable and incremental bending of surgical rod 90. In addition, first arm 14 further includes a first receiving portion 20 defining a U-shaped notch 20a configured to receive surgical rod 90 therein. At least a portion of engaging portion 18 and receiving portion 20 extend transversely outward from a longitudinal axis "A-A" defined by handle 12, thereby defining an acute angle with respect to longitudinal axis "A-A." For example the acute angle may range from about 10 degrees to about 60 degrees. In an embodiment, the acute angle may range from about 20 degrees to about 50 degrees. In another embodiment, the acute angle may range from about 30 degrees to about 40 degrees. Under such a configuration, when first and third receiving portions 20, 60 of first and second arm assemblies 10, 50 engage surgical rod 90 in the initial configuration, handles 12, 52 of first and second arm assemblies 10, 50 define a gap 102 therebetween.

With particular reference to FIGS. 1 and 6, second arm 30 of first arm assembly 10 includes a connecting portion 32 hingedly connected to hinge portion 16 of first arm 14. In particular, second arm 30 is detachably coupled to hinge portion 16 of first arm 14. Second arm 30 further includes an elongate body 34 extending between connecting portion 32 and a second receiving portion 36 defining a U-shaped notch 36a dimensioned to receive surgical rod 90 therein. Elongate body 34 and second receiving portion 36 define a longitudinal axis "Y-Y." Connecting portion 32 is slightly bent transversely outward, thereby defining an acute angle with respect to longitudinal axis "Y-Y". For example the acute angle may range from about 10 degrees to about 60 degrees. In an embodiment, the acute angle may range from about 20 degrees to about 50 degrees. In another embodiment, the acute angle may range from about 30 degrees to about 40 degrees. In addition, U-shaped notch 36a may be defined transverse to longitudinal axis "Y-Y."

With reference now to FIGS. 1, 4, and 5, second arm assembly 50 is substantially identical to first arm assembly 10. Identical constructions will not be described in detail to avoid obscuring the present disclosure in unnecessary detail. Second arm assembly 50 includes a handle 52, a first arm 54 extending from handle 52, and a second arm 80 detachably coupled with first arm 54. First arm 54 includes a hinge portion 56. Second arm 80 is hingedly connected with first arm 54 at hinge portion 56. First arm 54 further includes an engaging portion 58 having teeth 58a configured to engage engaging portion 18 of first arm 14 of first arm assembly 10 to enable stable and incremental bending of surgical rod 90. In addition, first arm 54 further includes a third receiving portion 60 defining a U-shaped notch 60a configured to receive surgical rod 90 therein. Handle 52 defines a longitudinal axis "B-B," and at least a portion of engaging portion 58 and third receiving portion 60 extend transversely outward, thereby defining an acute angle with respect to longitudinal axis "B-B". For example the acute angle may range from about 10 degrees to about 60 degrees. In an embodiment, the acute angle may range from about 20 degrees to about 50 degrees. In another embodiment, the acute angle may range from about 30 degrees to about 40 degrees. First and third receiving portions 20, 60 of first and second arm assemblies 10, 50 engage surgical rod 90 in the initial configuration and are transitioned to the first or second configuration to create a desirable bend in surgical rod 90. Handles 12, 52 of respective first and second arm assemblies 10, 50 define gap 102 therebetween in the initial configuration to facilitate relative movement of handles 12, 52.

With particular reference to FIGS. 1 and 6, second arm 80 of second arm assembly 50 includes a connecting portion 82 hingedly connected to hinge portion 56 of first arm 54. Second arm 80 further includes an elongate body 84 extending between connecting portion 82 and a fourth receiving portion 86 defining a U-shaped notch 86a dimensioned to receive surgical rod 90 therein. Elongate body 84 and fourth receiving portion 86 define a longitudinal axis "Z-Z." Connecting portion 82 defines an acute angle with respect to longitudinal axis "Z-Z." For example the acute angle may range from about 10 degrees to about 60 degrees. In an embodiment, the acute angle may range from about 20 degrees to about 50 degrees. In another embodiment, the acute angle may range from about 30 degrees to about 40 degrees. In addition, U-shaped notches 36a, 86a may be transversely defined with respect to respective longitudinal axes "Y-Y," "Z-Z", in opposite directions to further improve securement of surgical rod 90 received therein.

Figure 7:
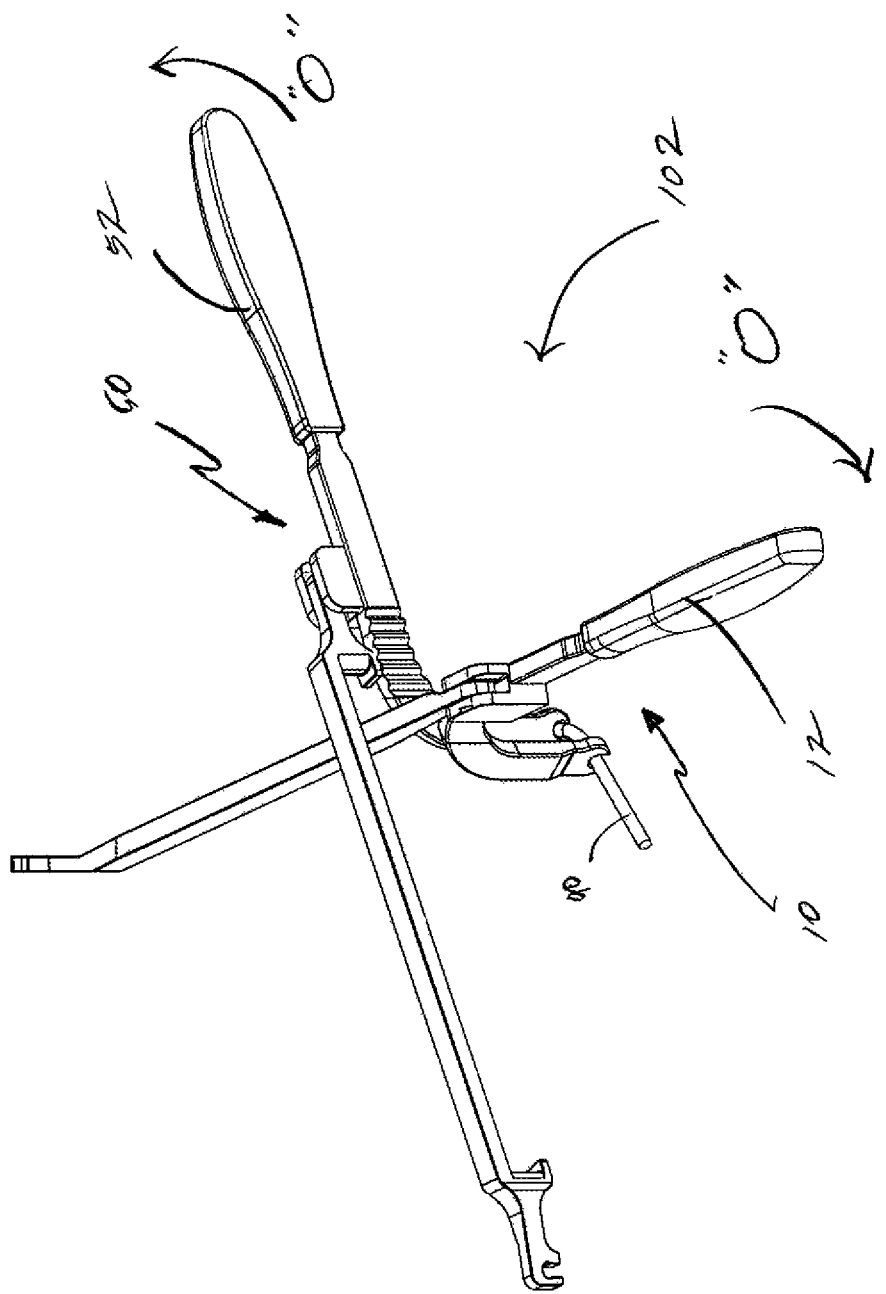
FIG. 7 is a perspective view of the instrument of FIG. 1 illustrating use in a second configuration.

In use, first and second arm assemblies 10, 50 may be selectively mated for a desired contour of surgical rod 90. For example, rod bender 100 may be placed in the initial configuration in which first and third receiving portions 20, 60 of respective first arms 14, 54 of first and second arm assemblies 10, 50 engage surgical rod 90 to create convex (FIG. 6) or concave (FIG. 7) bends in surgical rod 90. Initially, surgical rod 90 is positioned within U-shaped notches 20a, 60a of respective first and third receiving portions 20, 60 of first and second arm assemblies 10, 50. This can be done prior to surgical rod 90 being placed within the patient or in-situ. At this time, first and third receiving portions 20, 60 may be, e.g., in planar contact with or substantially parallel to, each other. Such placement of first and third receiving portions 20, 60 provides gap 102 between handles 12, 52, which facilitates manipulation of handles 12, 52. At this time, handles 12, 52 may be approximated towards each other in an inward direction as shown by arrows "I" (FIG. 1) to effect convex bending of surgical rod 90 (FIG. 6). Alternatively, handles 12, 52 may be approximated away from each other in an outward direction as shown by arrows "O" (FIG. 7) to effect concave bending of surgical rod 90 (FIG. 7). Under such a configuration, rod bender 100 may create a bend in surgical rod 90 that is, e.g., 90 degrees or more. It is contemplated that U-shaped notches 36a, 86a of second and fourth receiving portions 36, 86 of respective second arms 30, 80 of first and second arm assemblies 10, 50 may be utilized to created bends in surgical rod 90.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An instrument for bending a surgical rod comprising:
a first arm assembly including first and second arms, the first and second arms including respective first and second receiving portions configured to receive the surgical rod therein; and
a second arm assembly including third and fourth arms, the third and fourth arms including respective third and fourth receiving portions configured to receive the surgical rod therein, wherein the instrument is reconfigurable from an initial configuration in which the first and third receiving portions of the respective first and third arms engage the surgical rod such that approximating of the first and third receiving portions in a first direction bends the surgical rod in a first orientation and approximating of the first and third receiving portions in a second direction, different from the first direction, bends the surgical rod in a second orientation opposite to the first orientation.

2. The instrument according to claim 1, wherein the first and third receiving portions of the respective first and third arms of the first and second arm assemblies each define a notch configured to receive the surgical rod therein.

3. The instrument according to claim 1, wherein the surgical rod in the first orientation defines a convex profile.

4. The instrument according to claim 1, wherein the surgical rod in the second orientation defines a concave profile.

5. The instrument according to claim 1, wherein the first and third receiving portions in the initial configuration are in a planar contact.

6. The instrument according to claim 5, wherein the first and third arms of the first and second arm assemblies each include an L-shaped profile.

7. The instrument according to claim 1, wherein the second and fourth arms of the first and second arm assemblies are hingedly connected to the respective first and third arms of the first and second arm assemblies.

8. The instrument according to claim 1, wherein the first arm of the first arm assembly further includes a first handle, the first receiving portion of the first arm being offset from a longitudinal axis defined by the first handle.

9. The instrument according to claim 8, wherein the second arm of the second arm assembly further includes a second handle, wherein the first and third arms of the respective first and second arm assemblies include a mating structure to provide incremental approximating of the first and second handles.

10. The instrument according to claim 9, wherein the mating structure includes a plurality of teeth.

11. An instrument for bending a surgical rod comprising:
a first arm assembly including a first bend, a first plurality of teeth along the first bend, and a first receiving portion configured to receive the surgical rod therein, the first bend being unitary with the first receiving portion; and a second arm assembly including a second bend, a second plurality of teeth along the second bend, and a second receiving portion configured to receive the surgical rod therein, the second bend being unitary with the second receiving portion, the first and second arm assemblies detachably associated with each other through at least one tooth of each of the first plurality of teeth and the second plurality of teeth to provide incremental movement of the first arm assembly and second arm assembly, the instrument selectively configurable from an initial configuration to a first configuration in which the first and second receiving portions engage the surgical rod for bending the surgical rod in a first orientation, and from the initial configuration to a second configuration in which the first and second receiving portions engage the surgical rod for bending the surgical rod in a second orientation opposite to the first orientation.

12. The instrument according to claim 11, wherein the surgical rod in the first orientation defines a convex profile.

13. The instrument according to claim 11, wherein the surgical rod in the second orientation defines a concave profile.

14. The instrument according to claim 11, wherein the first and second receiving portions of the first and second arm assemblies each define a notch configured to receive the surgical rod therein.

15. The instrument according to claim 14, wherein the notches of the respective first and second receiving portions of the first and second arm assemblies are substantially parallel when the instrument is in the initial configuration.

16. The instrument according to claim 11, wherein the first and second arm assemblies each include a handle, the first and second receiving portions of the respective first and second arm assemblies being offset from respective longitudinal axes defined by the handles.

* * * * *